US011524129B2

(12) United States Patent
Säll et al.

(10) Patent No.: US 11,524,129 B2
(45) Date of Patent: Dec. 13, 2022

(54) AEROSOL GENERATOR WITH OBSTRUCTED AIR JETS

(71) Applicant: SHL MEDICAL AG, Zug (CH)

(72) Inventors: Daniel Säll, Segeltorp (SE); Stefan Gylleby, Akersberga (SE); Stuart Abercrombie, Milton (GB); Barry Brewster, Royston (GB); Charles Lowndes, Royston (GB); Steve Augustyn, Milton Keynes (GB); Oliver Harvey, Saffron Walden (GB); Benjamin Wicks, Histon (GB)

(73) Assignee: SHL MEDICAL AG, Zug (CH)

( * ) Notice: Subject to any disclaimer, the term of this patent is extended or adjusted under 35 U.S.C. 154(b) by 324 days.

(21) Appl. No.: 16/954,717

(22) PCT Filed: Jan. 10, 2019

(86) PCT No.: PCT/EP2019/050549
§ 371 (c)(1),
(2) Date: Jun. 17, 2020

(87) PCT Pub. No.: WO2019/145159
PCT Pub. Date: Aug. 1, 2019

(65) Prior Publication Data
US 2020/0384217 A1 Dec. 10, 2020

(30) Foreign Application Priority Data
Jan. 23, 2018 (EP) .................................... 18152985

(51) Int. Cl.
*A61M 15/00* (2006.01)
*A61M 11/00* (2006.01)
*A61M 11/08* (2006.01)

(52) U.S. Cl.
CPC ........ *A61M 15/009* (2013.01); *A61M 11/002* (2014.02); *A61M 11/006* (2014.02);
(Continued)

(58) Field of Classification Search
CPC .. A61M 11/002; A61M 11/006; A61M 11/02; A61M 11/08; A61M 15/002;
(Continued)

(56) References Cited

U.S. PATENT DOCUMENTS 1,751,787 A * 3/1930 Binks ...................... B05B 7/083
239/301
2,235,708 A * 3/1941 Jenkins ................. B05B 7/0815
239/296
(Continued)

FOREIGN PATENT DOCUMENTS

CN 204352320 U 5/2015
CN 105209096 A 12/2015
(Continued)

OTHER PUBLICATIONS

International Search Report and Written Opinion for Int. App. No. PCT/EP2019/050549, completed Mar. 18, 2019.

*Primary Examiner* — Kathryn E Ditmer
(74) *Attorney, Agent, or Firm* — McDonnell Boehnen Hulbert & Berghoff LLP

(57) ABSTRACT

An aerosol generator for an aerosol dispenser is presented where, the aerosol generator has a housing having an inlet part comprising a liquid inlet configured to guide a liquid jet (L) into the housing and an air inlet configured to guide an air flow into the housing. The housing further having an outlet part having an aerosol outlet configured to guide an aerosol (C) of liquid mixed with air out of the housing. The air inlet is configured such that at least part of the air flow entering the housing through the air inlet is obstructed at a
(Continued)

distance from the liquid jet (L) entering the housing through the liquid inlet, thereby creating a source of turbulence in the housing to interact with droplets of the liquid jet (L) to prevent coalescence of the droplets.

16 Claims, 9 Drawing Sheets

(52) U.S. Cl.
CPC .......... *A61M 11/08* (2013.01); *A61M 15/002* (2014.02); *A61M 15/0021* (2014.02); *A61M 2206/14* (2013.01); *A61M 2210/0612* (2013.01)

(58) Field of Classification Search
CPC ... A61M 15/009; A61M 2206/14; B05B 1/00; B05B 1/02; B05B 1/06; B05B 1/10; B05B 1/26; B05B 1/3421; B05B 1/3426; B05B 7/0012; B05B 7/0075; B05B 7/0416; B05B 7/0458; B05B 7/0475; B05B 7/0483; B05B 7/0807; B05B 7/0861
See application file for complete search history.

(56) References Cited

U.S. PATENT DOCUMENTS

| | | | | | |
|---|---|---|---|---|---|
| 2,323,464 | A * | 7/1943 | Glessner | B05B 1/1609 | 239/443 |
| 2,772,117 | A * | 11/1956 | Ritzau | A61M 11/002 | 239/524 |
| 3,761,065 | A * | 9/1973 | Rich | B01F 25/27 | 261/DIG. 42 |
| 3,848,807 | A * | 11/1974 | Partida | B05B 7/0075 | 239/296 |
| 3,923,251 | A * | 12/1975 | Flournoy | B05B 7/10 | 431/351 |
| 4,120,640 | A * | 10/1978 | Martin | F23M 9/06 | 431/353 |
| 4,899,937 | A * | 2/1990 | Haruch | B05B 12/088 | 239/289 |
| 4,945,929 | A | 8/1990 | Egilmex | | |
| 5,256,352 | A * | 10/1993 | Snyder | B05B 7/065 | 261/78.2 |
| 5,344,078 | A * | 9/1994 | Fritz | B05B 7/0815 | 239/296 |
| 5,954,047 | A * | 9/1999 | Armer | A61M 15/0095 | 128/200.14 |
| 6,248,378 | B1 | 6/2001 | Ganan-Calvo | | |
| 6,367,471 | B1 * | 4/2002 | Genosar | A61M 15/0086 | 128/200.14 |
| 6,615,826 | B1 * | 9/2003 | Gabrio | A61M 15/0096 | 128/200.14 |
| 6,629,524 | B1 * | 10/2003 | Goodall | A61M 15/0065 | 239/338 |
| 7,905,229 | B2 * | 3/2011 | Giroux | A61M 15/0021 | 128/200.21 |
| 9,216,259 | B2 * | 12/2015 | Kakade | A61M 15/0021 | |
| 2006/0096589 | A1 * | 5/2006 | Djupesland | A61M 15/0086 | 128/200.14 |
| 2009/0026291 | A1 * | 1/2009 | Shimada | B05B 7/066 | 239/405 |
| 2009/0050137 | A1 * | 2/2009 | Wissink | A61M 15/009 | 128/200.14 |
| 2009/0173807 | A1 | 7/2009 | Chang | | |
| 2010/0276507 | A1 * | 11/2010 | Labegorre | B05B 7/10 | 239/11 |
| 2012/0018525 | A1 | 1/2012 | Giroux et al. | | |
| 2012/0104119 | A1 | 5/2012 | Benalikhoudja | | |
| 2013/0306061 | A1 | 11/2013 | Kakade | | |
| 2014/0076308 | A1 | 3/2014 | Dunne | | |
| 2014/0263190 | A1 * | 9/2014 | Biberger | C23C 4/134 | 219/68 |
| 2016/0015912 | A1 * | 1/2016 | De Kruijf | A61M 11/006 | 128/200.21 |
| 2017/0143915 | A1 | 5/2017 | Strange et al. | | |

FOREIGN PATENT DOCUMENTS

| | | | | |
|---|---|---|---|---|
| CN | 206414576 U | 8/2017 | | |
| CN | 107497021 A | 12/2017 | | |
| EP | 0839544 A2 | 5/1998 | | |
| EP | 1591137 A2 | 11/2005 | | |
| JP | 2002-537077 A | 11/2002 | | |
| NL | 2023033 B1 | * | 11/2020 | A61M 11/002 |
| WO | WO-8101186 A | * | 4/1981 | B05B 1/3405 |
| WO | 2003084591 A1 | 10/2003 | | |
| WO | WO-2004020111 A1 | * | 3/2004 | B05B 7/0861 |
| WO | WO-2007106686 A2 | * | 9/2007 | A61M 11/002 |
| WO | 2008/017575 A1 | 2/2008 | | |
| WO | 2014/137215 A1 | 9/2014 | | |

* cited by examiner

AEROSOL GENERATOR WITH OBSTRUCTED AIR JETS

CROSS REFERENCE TO RELATED APPLICATIONS

The present application is a U.S. National Phase Application pursuant to 35 U.S.C. § 371 of International Application No. PCT/EP2019/050549 filed Jan. 10, 2019, which claims priority to European Patent Application No. 18152985.0 filed Jan. 23, 2018. The entire disclosure contents of these applications are herewith incorporated by reference into the present application.

TECHNICAL AREA

The present disclosure relates to an aerosol generator for an aerosol dispenser, and more particularly to an aerosol generator for preventing coalescence of droplets of the aerosol.

BACKGROUND

Most inhalation devices are today based on inhalation of a dry powder medicament or on aerosolization of a metered dose of a liquid drug, e.g. Metered Dose Inhalers (MDI).

A dry drug may be stored for long periods of time without deteriorating, and the particles may be small to reach delivery targets deep in the lungs. However, there are several drawbacks, such as adhesion of powder in the mouth and in the throat of a user. There are also formulations which are not suitable for a dry powder.

Metered Dose Inhalers are based on delivery of an aerosolized medicine which is dissolved or suspended in a propellant gas. The use of a propellant causes deposition of droplets in the mouth and/or throat of the user. The user also has to be careful to inhale at the same time as the MDI device is actuated. Furthermore, the droplets generated by an MDI are on average relatively large and may not be able to reach the optimal delivery sites deep in the lungs.

Attempts have been made to generate an aerosol which may be inhaled without a propellant. To this end, it is necessary to generate a cloud of droplets in which the droplets are prevented from coalescing. Such an aerosol may also be used as an eye spray, provided that the aerosol may be drive forward by other means than the inhalation of air. WO2014/137215 shows an aerosol generator having a nozzle which generates a Rayleigh droplet train. Droplets in the front of the train are slowed down by air in the mixing chamber. Droplets behind, however, are caught in the slipstream and will therefore catch up with the droplets ahead, causing coalescence and increasing droplet sizes. To prevent coalescence, intake ducts for air are directed towards the droplet train such that air streams impinge on each other in the droplet train, thereby disturbing the train of droplets to displace the droplets and consequently reduce the slipstream effect.

SUMMARY

In the present disclosure, when the term "distal" is used, this refers to the direction pointing away from the dose delivery site. When the term "distal part/end" is used, this refers to the part/end of the dispenser/delivery device, or the parts/ends of the members thereof, which under use of the dispenser/delivery device is/are located furthest away from the dose delivery site. Correspondingly, when the term "proximal" is used, this refers to the direction pointing to the dose delivery site. When the term "proximal part/end" is used, this refers to the part/end of the dispenser/delivery device, or the parts/ends of the members thereof, which under use of the dispenser/delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

In view of the foregoing, a general object of the present disclosure is to provide an aerosol generator showing an improved aerosolization of a liquid medicament and a reduction of the coalescence of droplets of the generated aerosol.

According to a main aspect of the disclosure it is characterised by an aerosol generator for an aerosol dispenser, which aerosol generator comprises a housing having an inlet part comprising a liquid inlet configured to guide a liquid jet into the housing, the liquid inlet (16) comprising a nozzle (20) having a micro-structured aperture configured to generate a liquid jet (L) in the form of a Rayleigh droplet train from a pressurised liquid (24) which is forced through said aperture upon activation of an aerosol dispenser, the housing further comprises an air inlet configured to guide an air flow into the housing, and an outlet part comprising an aerosol outlet configured to guide an aerosol, comprising liquid mixed with air, out of the housing; wherein the air inlet is directed such that at least part of the air flow entering the housing through the air inlet during activation of an aerosol dispenser is guided to be obstructed at a distance from the liquid jet entering the housing through the liquid inlet, thereby creating a source of turbulence in the housing to interact with droplets of the liquid jet to prevent coalescence of the droplets.

It has been shown that instead of colliding air streams in the liquid jet or droplet train, a more even and larger spread of turbulence is achieved by creating multiple sources of turbulence by obstructing the air flow at a distance from the liquid jet/droplet train. By obstructing is meant that the air flow is not allowed to interact with the liquid jet directly. Instead, the air flow encounters an obstruction before impinging on the liquid jet, or before passing the liquid jet. The obstruction may be another flow of air crossing the path of the air flow, or a physical structure in the path of the air flow. Furthermore, the air flow, or air jets move slower, which allows the droplets to spend more time in the turbulence and spread out more before exiting through the aerosol outlet.

Generation of Rayleigh droplet trains is known from prior art. By correctly configuring the aperture dimensions and the pressure of the liquid pushed through the aperture, the Rayleigh droplet train will form spontaneously as it exits the aperture.

According to another aspect of the disclosure the air inlet comprises a first inlet guide for distributing a turbulence-generating air flow and a second inlet guide for distributing a sheath air flow.

Thus the inhaled air is divided between the turbulence-generating air flow and the sheath air flow.

According to another aspect of the disclosure the first inlet guide comprises multiple orifices through which said turbulence-generating air flow is distributed into multiple air jets, and the multiple air jets generate multiple sources of turbulence distributed in the housing, each source of turbulence located at a distance from the liquid jet.

The multiple air jets are used to create multiple sources of turbulence, thereby creating a larger area or volume of turbulence in the housing.

According to another aspect of the disclosure each of said air jets is directed to be obstructed by collision with at least one other air jet at a distance from said liquid jet, such that a source of turbulence is generated offset from the liquid jet.

In one embodiment, the sources of turbulence are created by colliding air jets with each other.

According to another aspect of the disclosure each of said air jets is set to be obstructed by collision with a structure comprised in the housing at a distance from said liquid jet.

In this embodiment, the sources of turbulence are created by colliding the air jets with physical obstacles in the housing, which obstacles are located at a distance from the liquid jet.

According to another aspect of the disclosure the liquid jet is directed substantially orthogonally to an inlet plane, and wherein the first inlet guide is configured to direct the multiple air jets at angles relative to the inlet plane. The liquid jet may furthermore be directed substantially along an axis L, and the multiple orifices of the first inlet guide may be distributed along the axis L.

In this way, sources of turbulence may be generated and spread out over the whole volume of the housing. The air jets may also be directed at an angle against or along the direction of flow of the liquid jet, which may further affect the spread of the droplets in the housing.

According to another aspect of the disclosure the liquid jet is directed substantially along an axis L, and wherein the multiple orifices of the first inlet guide are distributed in a plane parallel to the inlet plane.

The orifices may thus be placed in a plane at any position along the liquid jet. The orifices may also be placed in the plane comprising the liquid inlet itself.

According to another aspect of the disclosure the liquid jet only indirectly interacts with the air flow via turbulence generated by the source of turbulence.

Basically, the gist of this disclosure is the indirect disturbance of the liquid jet, or the droplet train, so that the droplets spread out more and coalesce less.

According to another aspect of the disclosure the second inlet guide comprises an elongated orifice along an inner perimeter of the housing, which elongated orifice, is configured to distribute a sheath air flow along an inner surface of the housing in a direction towards the aerosol outlet.

The sheath air flow is configured to achieve a flow of air along the inner surfaces of the housing so that the droplets are prevented from adhering to the surfaces.

According to another aspect of the disclosure the nozzle comprises multiple micro-structured apertures for generating multiple Rayleigh droplet trains.

Generally, multiple apertures are used to create multiple droplet train in order to be able to deliver a larger dose per time unit.

According to another aspect of the disclosure the housing is connected to a mouthpiece of an inhaler and the air flow is generated by a user inhaling air through the mouthpiece.

As previously stated, the air flow needed to generate the aerosol for inhalation is generated by the user of the device, as he or she inhales through the mouthpiece. Consequently, no additional propellant is required to drive the aerosol out of the housing.

According to another aspect of the disclosure the housing is connected to an eyepiece of an eye spray device or an inhalation device for children and wherein the air flow is generated by pressurised gas, such as pressurised air, actuated by a user.

Since the aerosol generated by means of the present disclosure may be applied for treating eye afflictions, a delivery device having an additional propellant, activated by the user, is conceivable. Also, since children may have difficulties following instructions for how to use inhalation breath to create the aerosol in an efficient manner, inhalation devices for children are often equipped with such an additional propellant.

BRIEF DESCRIPTION OF DRAWINGS

In the following detailed description of the disclosure, reference will be made to the accompanying drawings, of which

DETAILED DESCRIPTION

Figure 1:
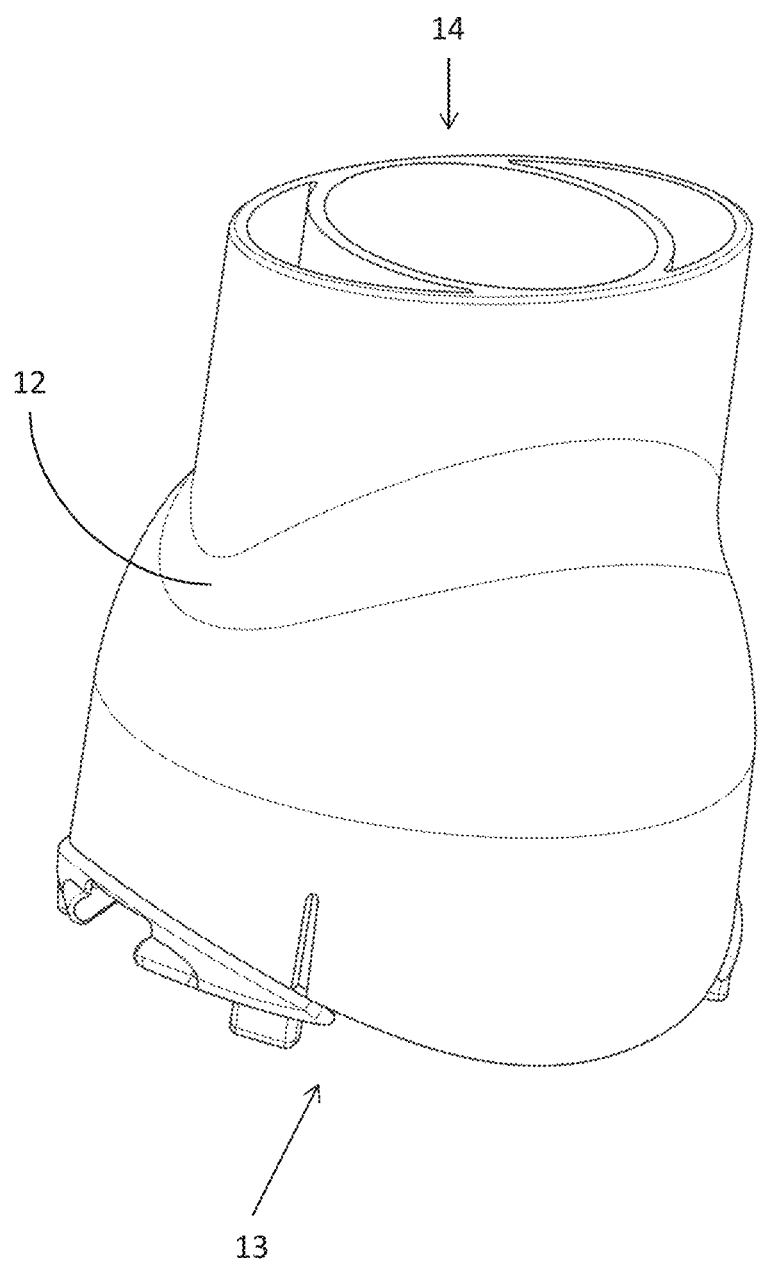
FIG. 1 shows a mouthpiece for an inhalation device.

The present disclosure relates to an aerosol generator 10 for use in an aerosol dispenser, such as an inhalation device or an eye spray device. An exemplary mouthpiece for an inhalation device is shown in FIG. 1. The mouthpiece comprises a housing 12, having an inlet part 13, which may be connected to a housing part of the aerosol dispenser (not shown), and an outlet part 14 configured to be inserted into the mouth of a user. The aerosol generator is contained in the housing 12, as will be described below.

Figure 2:
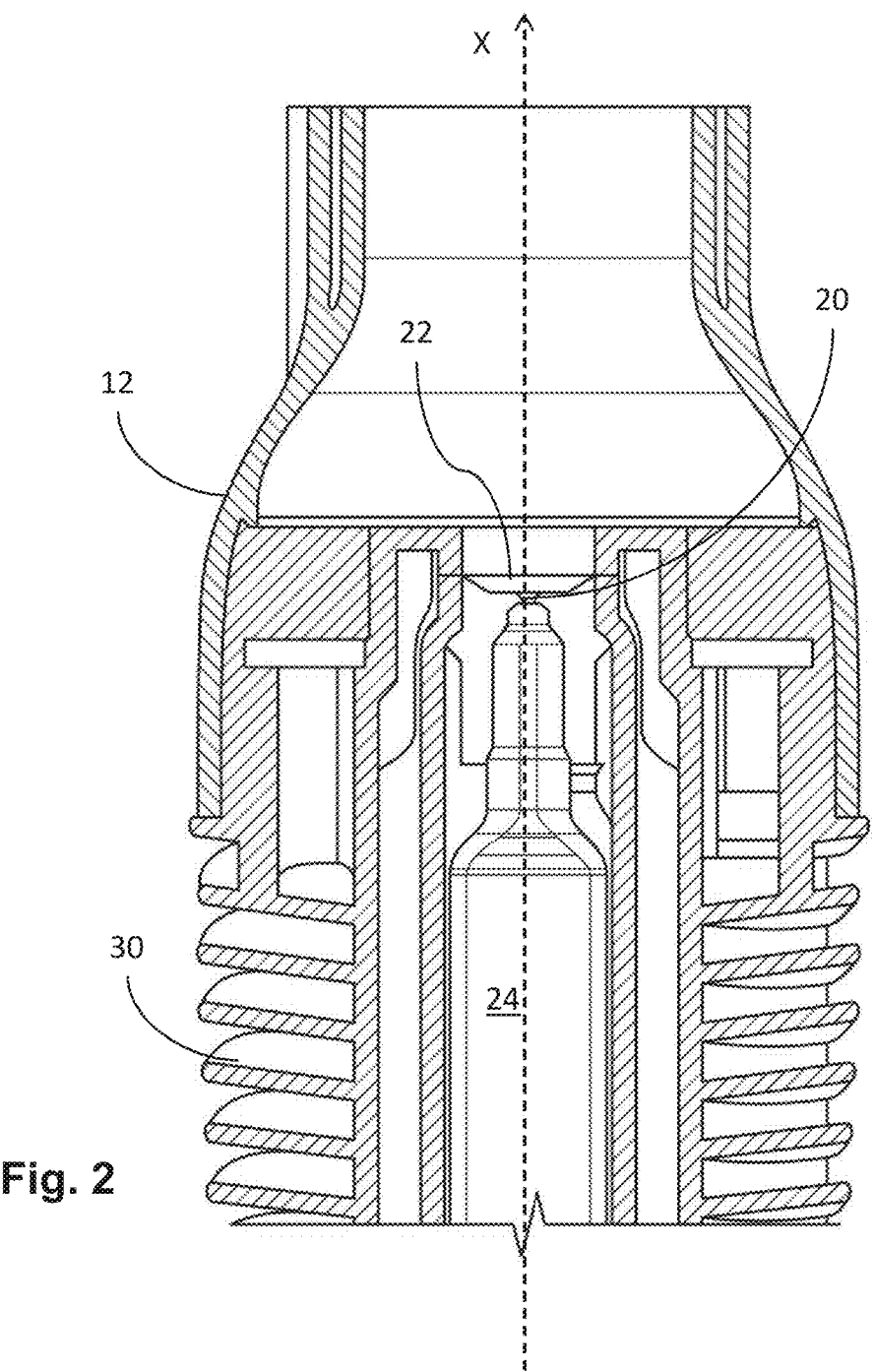
FIG. 2 is a cross-sectional view of the mouthpiece of FIG. 1, as attached to a front housing of an aerosol dispenser.

FIG. 2 shows a cross-section of the aerosol generator 10 of FIG. 1, when attached to a front housing 30 of the aerosol dispenser. The housing 12 is exemplified as the mouthpiece of an inhalation device. A nozzle 20, configured to generate a Rayleigh droplet train, is fixedly arranged in a nozzle holder 22. The nozzle may be a micro-machined ceramic die having through-going micro apertures extending through the die. When activated for dose delivery, a drive mechanism (not shown) may be arranged to pressurise a liquid medicament, held in a medicament container 24 in the front housing 30, such that the medicament is forced through the apertures of the nozzle 20, thereby creating a liquid jet L (FIG. 3), travelling along an axis X, which is substantially orthogonal to an outlet surface of the nozzle 20. The outlet surface of the nozzle 20 is thus defined as an inlet plane.

The liquid jet L spontaneously breaks up into a Rayleigh droplet train as a function of liquid pressure, liquid viscosity and aperture dimensions. The generation of the Rayleigh droplet train is not an object of the present disclosure. It is known, however, that for medicaments of interest for inhalation and eye spray applications, liquid pressure is preferably between 2 and 60 Bar, and the aperture dimensions, e.g. diameter, of the nozzle is preferably between 0.5 and 5 micrometers.

Figure 3:
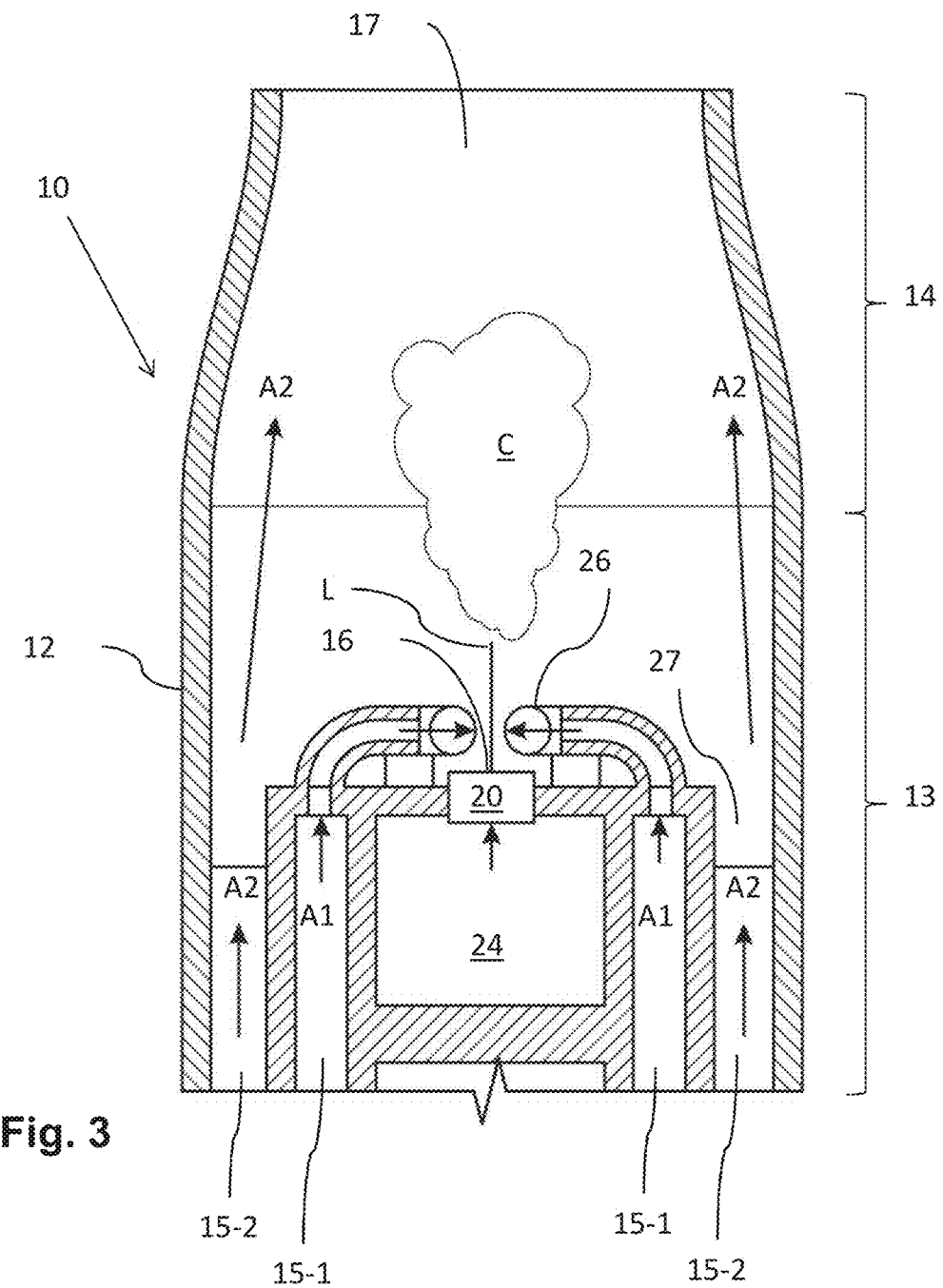
FIG. 3 is a cross-sectional, conceptual, view of the mouthpiece and aerosol generator of FIGS. 1 and 2.

FIG. 3 shows a conceptual cross-sectional view of the aerosol generator 10 of FIG. 2, which aerosol generator 10 comprises the housing 12 having the inlet part 13 comprising a liquid inlet 16 configured to guide the liquid jet L into the housing and an air inlet 15 configured to guide an air flow A into the housing 12. As mentioned above, the aerosol dispenser may for instance be a medicament delivery device, such as an inhalation device or an eye spray device. The housing 12 further has the outlet part 14 which comprises an aerosol outlet 17 configured to guide an aerosol C, comprising liquid mixed with air, out of the housing 12. The air inlet 15 is configured such that at least part of the air flow A entering the housing 12 through the air inlet 15 is obstructed at a distance from the liquid jet L, which enters the housing 12 through the liquid inlet 16. By obstructing is meant that the air flow is not allowed to interact with the liquid jet directly. Instead, the air flow encounters an obstruction before impinging on the liquid jet, or before passing the liquid jet. The obstruction may be another flow of air crossing the path of the air flow, or a physical structure in the path of the air flow. The obstruction creates a source of turbulence in the housing 12 to interact with droplets of the liquid jet L to prevent coalescence of the droplets.

The liquid inlet 16 may be the aperture(s) of the nozzle 20. As the fluid medicament of the container 24 is pressurised and forced through the nozzle, the fluid medicament enters the housing 12 as a liquid jet L, which breaks up into one or more Rayleigh droplet trains. There is at least one aperture provided in the nozzle 20. Preferably, an array of apertures is provided, such that multiple Rayleigh droplet trains are generated.

The droplets of the train(s) have a certain forward velocity, but due to air resistance, droplets at the front of the train lose some velocity, while the droplets behind are caught in the slipstream and catch up with droplets ahead, causing coalescence and an increase in the average size distribution of the droplets. It is therefore an object of the present disclosure to prevent, or reduce, the coalescence of the droplets.

As shown in FIG. 3, the air inlet 15 comprises a first inlet guide 15-1 for distributing a turbulence-generating air flow A1 and a second inlet guide 15-2 for distributing a sheath air flow A2. The sheath air flow A2 is guided along inner walls of the housing 12, via at least one elongated orifice 27 along an inner perimeter of the housing 12, such as to prevent droplets of the generated aerosol C from adhering to the walls before the aerosol is entrained out of the housing 12 through the aerosol outlet 17. The turbulence-generating air flow A1 may be divided into multiple turbulence-generating air jets a1 which enter the housing 12 via orifices 26.

The conceptual FIG. 3 may represent a view of the second embodiment shown in FIGS. 7a-7d and FIG. 8, wherein the air jets a1 are collided with each other to generate turbulence, which will be described in detail below.

It is generally known that high inhalation speeds affect the amount of deposition of the inhaled drug on surfaces which are not the target of the medical treatment, such as deposition in the user's mouth, on the tongue and in the throat. Slow inhalation allows more of the medicament to reach target sites in the lower part of the lungs. The present aerosol generator is thus a promising means for allowing slow inhalation, since a slow-moving aerosol C is generated in the housing 12, which aerosol may then be inhaled by the user at a comfortable and effective rate.

Another important factor influencing the delivery to the target sites is the size of the droplets. Smaller droplets may reach deeper into the lungs. Earlier attempts have sought to reduce the average size of the droplets by either impinging liquid jets on one another at high pressure to create smaller droplets, or by impinging air jets directly on the liquid jet in order to cause turbulence and reduce coalescence in the Rayleigh droplet trains. The latter technique has shown some promise. However, a number of problems remain.

The known technique of impinging air jets on the liquid jet(s) results in a rather localised source of turbulence, which is not very efficient at spreading out the droplets since the droplets do not spend enough time in the limited turbulent space. In addition, the air jets travel toward the liquid jets at rather high velocity, which may cause delamination of the sheath air from the walls of the housing 12, which may in turn cause increased deposition of droplets on the housing walls.

The work forming the basis for the present disclosure has shown that these problems may be mitigated, or solved, by spreading or increasing the turbulence in the housing 12, and also by slowing down the turbulence-generating air flow A1 in the housing 12. In this way, the droplets spend a longer time in the turbulent space, and the lower speed of the air jets a1 causes less delamination of the sheath airflow A2 from the walls of the housing.

The effect is achieved by obstructing the turbulence-generating air flow A1, either by arranging physical obstructions in the paths of the air jets a1, at a distance from the liquid jet(s), or by colliding the air jets a1 with one another at a distance from the liquid jet(s). The obstructions generate sources of turbulence in the housing 12, which increase the spread of turbulent space and thus the time that the droplets spend in the turbulent space, exposed to the turbulence.

The obstructions of the air jets a1 also slows down their speeds, thereby improving, i.e. reducing, the delamination of the sheath air flow A2 from the walls of the housing 12.

The distance between the liquid jet(s) and the obstructions may be varied, depending on various factors, but studies have shown that the air jets a1 should preferably not be aimed directly at the liquid jet(s), because direct impingement of the air jets a1 on the liquid jet(s) may cause a certain increase in coalescence as droplets are pushed together with droplets of neighbouring liquid jets. For instance, the direction of flow of an air jet a1 may be aligned with a row of nozzle apertures such that droplets of a liquid jet exiting one aperture is pushed into the droplets of a liquid jet exiting a neighbouring aperture. Accordingly, the liquid jet L only indirectly interacts with the turbulence-generating air flow A1.

The expressions "at least at a distance" or "at a distance", used herein, mean that orifices 26 (FIG. 3), which guide the air jets a1, are configured such that the air jets a1 are guided to interact with an obstruction at a distance, e.g. offset, from the liquid jet L. In other words, only turbulent or obstructed air interacts with the liquid jet L.

Figure 4A:
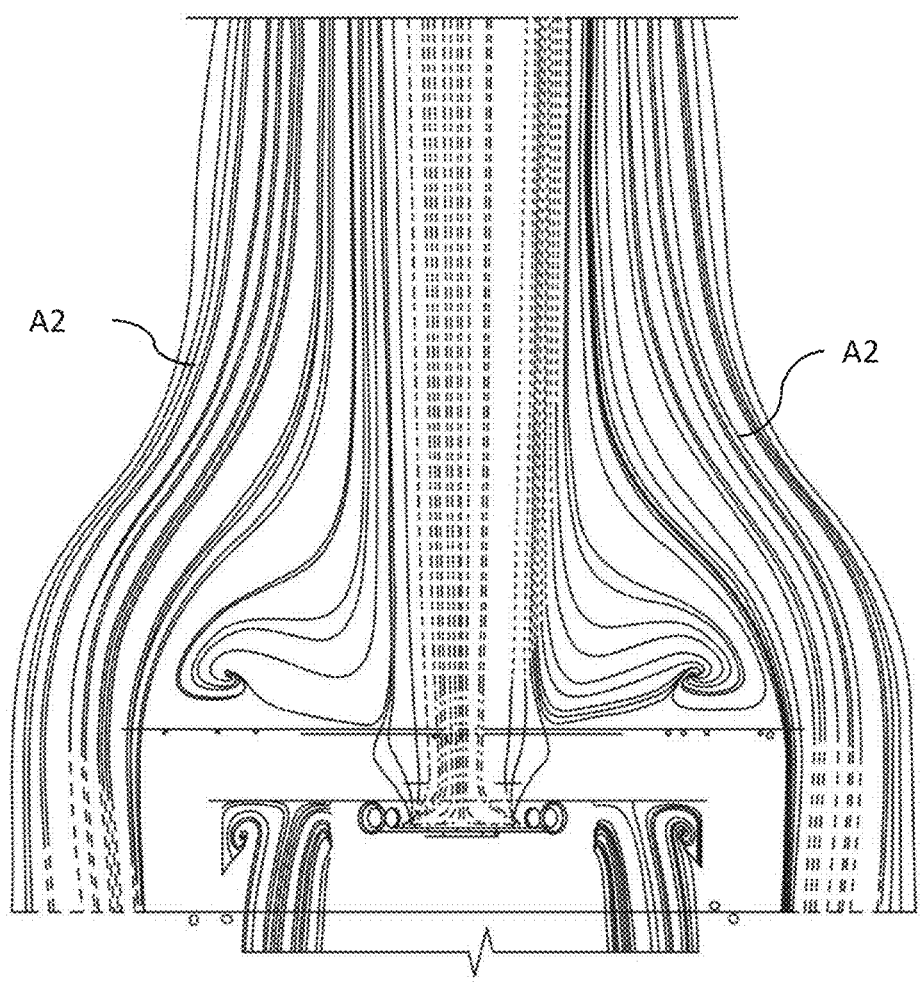
FIG. 4A is a simulation of air flow in the mouthpiece according to the present disclosure.

FIG. 4a shows a simulation of the present aerosol generator, wherein the turbulence-generating air flow A1 is shown to be slow-moving compared to prior art, which causes the turbulence to spread out quickly to fill a full diameter of the housing. The sheath air flow A2 is further shown to adhere well to the walls of the housing 12.

Figure 4B:
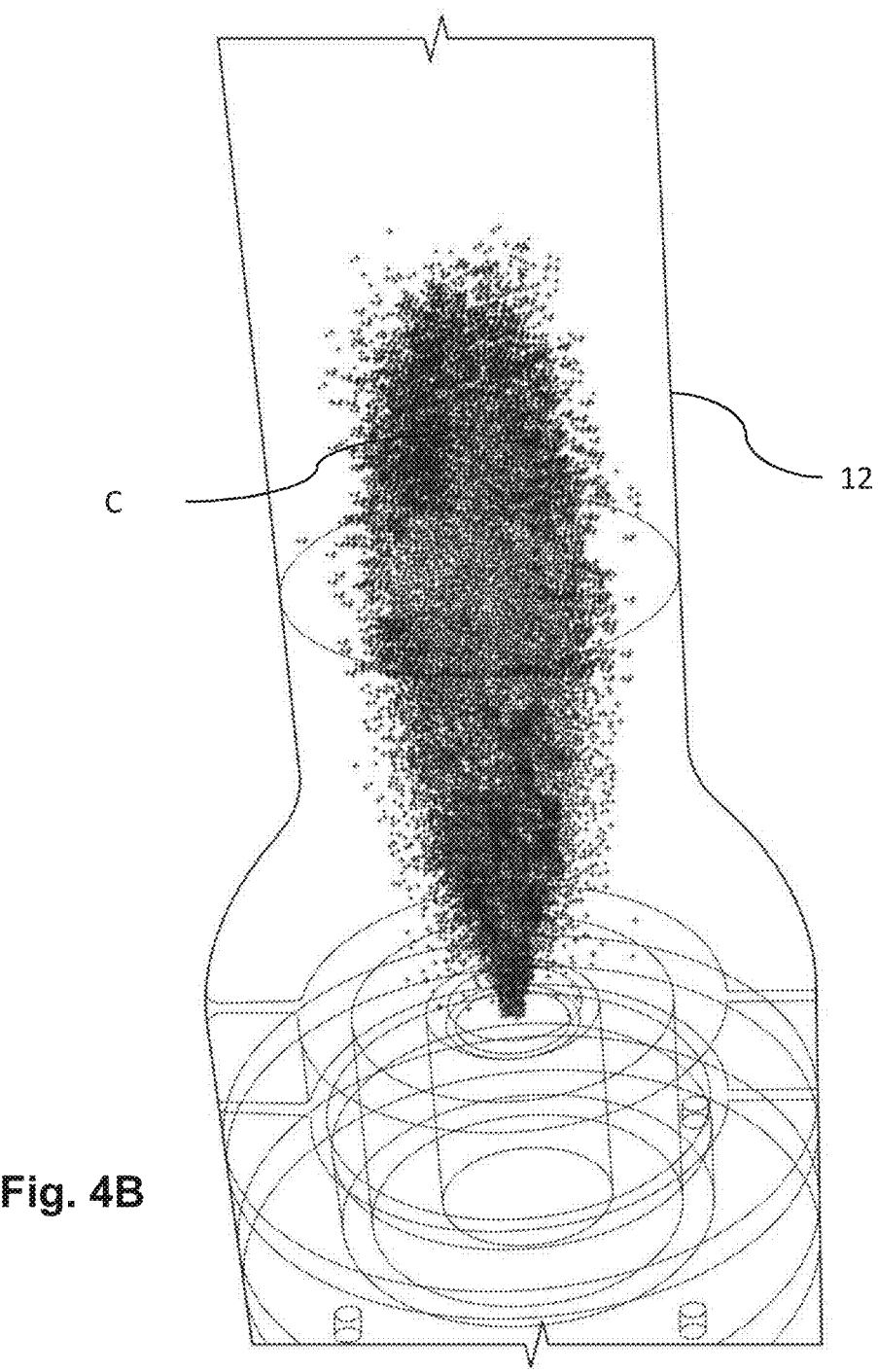
FIG. 4B is a simulation of the distribution of an aerosol in the mouthpiece according to the present disclosure.

FIG. 4b shows a distribution of the droplets of the aerosol C in the housing 12. The droplets are shown to initially spread quickly and then maintain a relatively constant profile. No droplets approach the housing wall, indicating excellent sheath flow behaviour.

In a first embodiment of the present disclosure, the air jets a1 of the turbulence-generating air flow A1 are obstructed by physical obstacles 25, such as pillars, protrusions, bumps, etc, which are placed between the orifices 26 and the liquid inlet 16 of the nozzle 20. As mentioned previously, the liquid inlet may comprise multiple apertures, each guiding a liquid jet L into the housing 12.

Figure 5A:
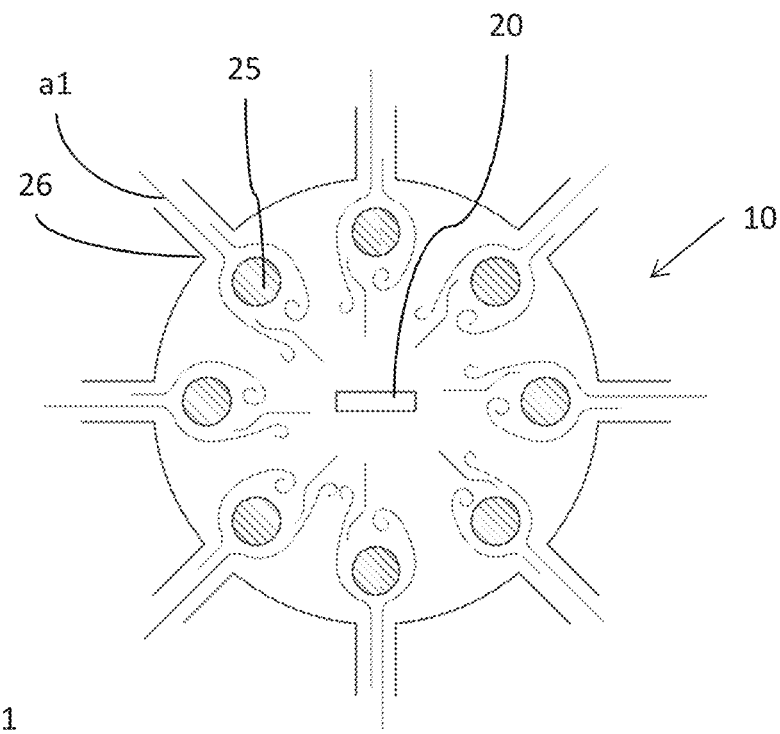
FIG. 5A shows turbulence generation according to a first embodiment of the present disclosure.

FIG. 5a shows a conceptual cross-sectional view of the aerosol generator 10, as seen from the outlet part 14. The orifices 26 guide the air jets a1 towards the liquid jet L (not shown), which is expelled from the nozzle 20. An obstruction in the form of a physical obstacle 25 is arranged between each orifice 26 and the nozzle 20. An air jet a1 colliding with the obstruction generates a source of turbulence, which results in turbulent air around the obstruction. Thus, multiple sources of turbulence may form a larger area, or volume, of turbulent air in the housing 12. In order to avoid direct interaction between the liquid jet 16 and the air jets a1, each source of turbulence, i.e. each obstruction, is configured to be located at least at a distance from the liquid jet. Also, the obstruction is formed so that direct flow from the orifice 26 towards the liquid jet is prevented. In the example shown, the diameter of the orifice 26 is 0.40 mm and the diameter of the obstruction is 0.75 mm.

Figure 5B:
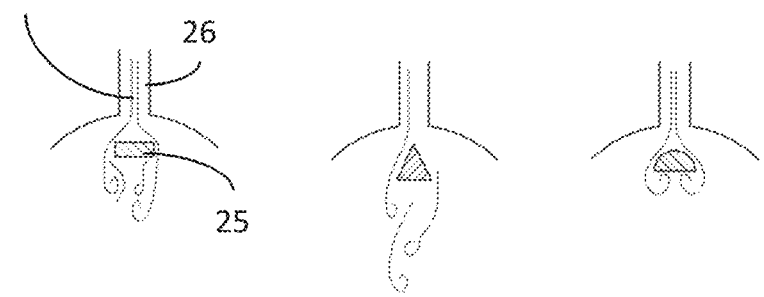
FIG. 5B shows turbulence generation according to a first embodiment of the present disclosure.

FIG. 5b shows three examples of shaped obstacles 25. The shape may affect the spread of the turbulence around the obstacles. However, initial studies have shown that the influence of the shape on the turbulence is not significant.

Figure 5C:
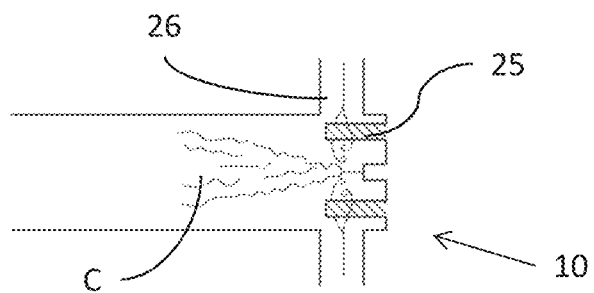
FIG. 5C shows turbulence generation according to a first embodiment of the present disclosure.

FIG. 5c shows a cross-sectional side view of the turbulence generator of FIG. 5a. It is shown how the air jets a1 are obstructed by the obstacles 25 and how the turbulence affects the droplet trains to spread the droplets and form the aerosol C.

Figure 6:
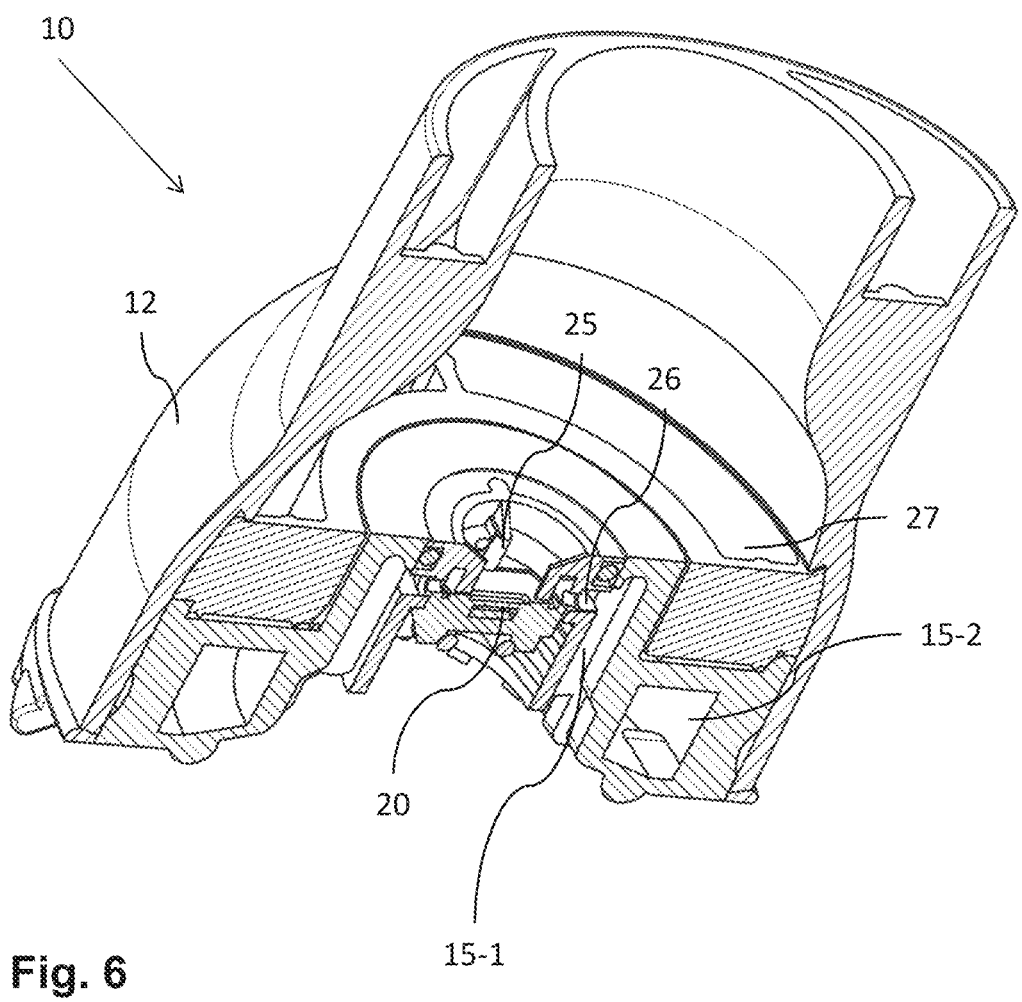
FIG. 6 is a cross-sectional view of a first embodiment of the present disclosure.

FIG. 6 shows a perspective cross-sectional view of the aerosol generator 10 of FIG. 5a. The obstacles 25 are shown as pillars arranged between the orifices 26 and the nozzle 20. It is also exemplified how the first inlet guides 15-1 and the second inlet guides 15-2 may be arranged to provide the turbulence-generating airflow A1 and the sheath airflow A2.

Figure 7A:
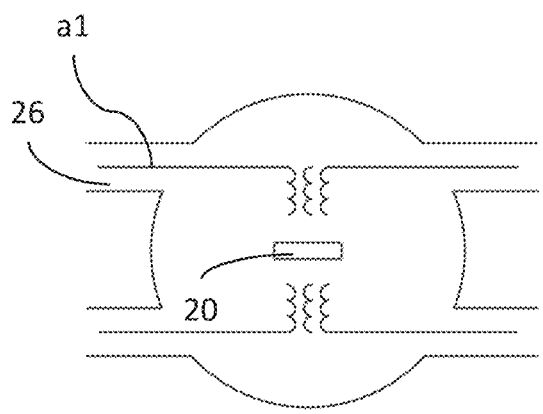
FIG. 7A shows turbulence generation according to a second embodiment of the present disclosure.
Figure 7B:
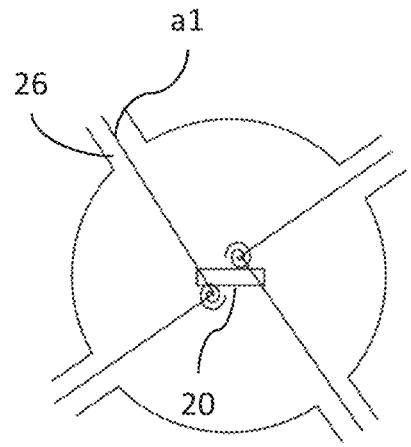
FIG. 7B shows turbulence generation according to a second embodiment of the present disclosure.
Figure 7C:
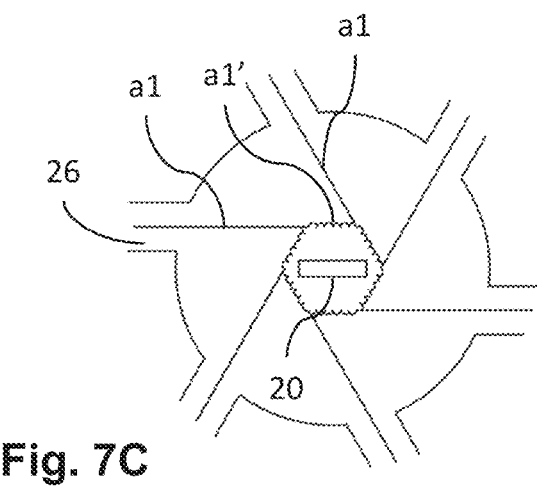
FIG. 7C shows turbulence generation according to a second embodiment of the present disclosure.
Figure 7D:
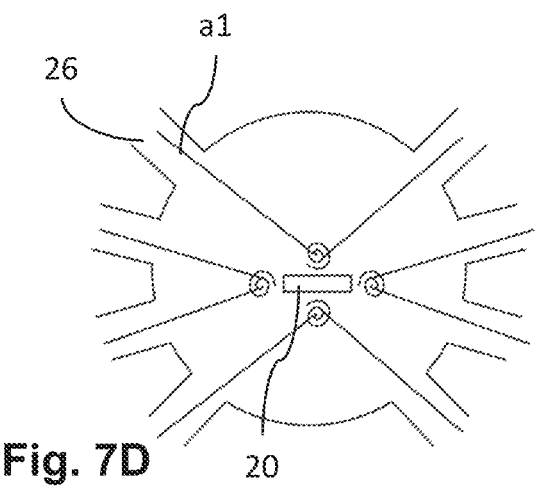
FIG. 7D shows turbulence generation according to a second embodiment of the present disclosure.
Figure 8:
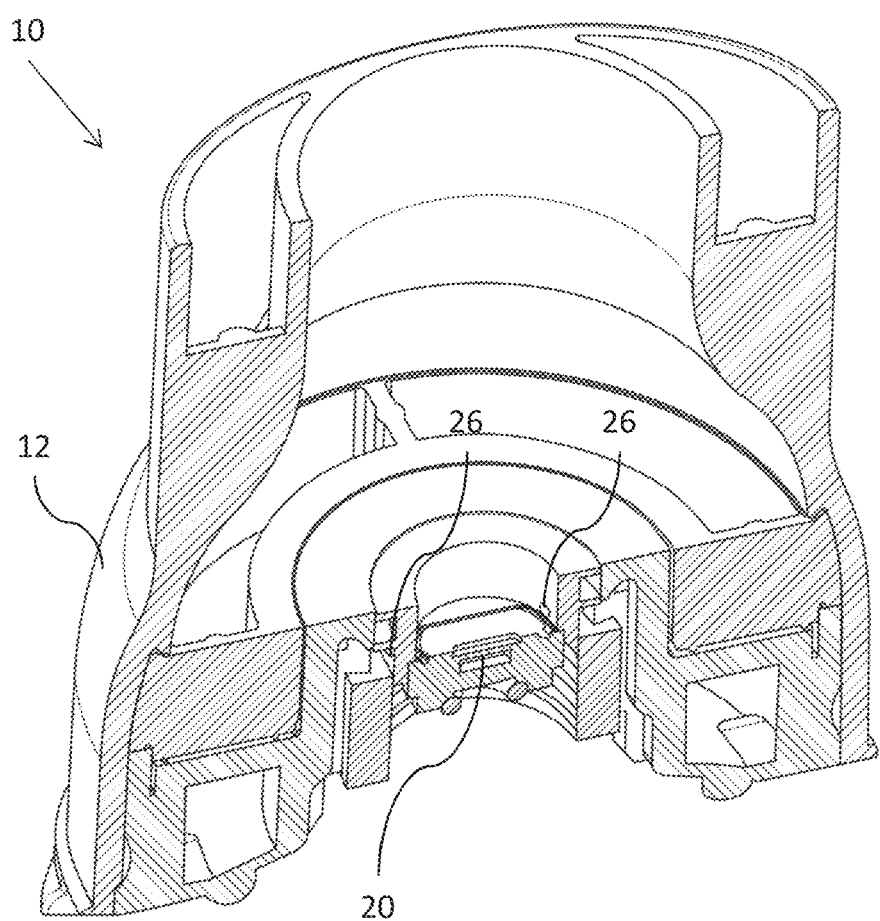
FIG. 8 is a cross-sectional view of a second embodiment of the present disclosure.

In a second embodiment, shown in FIGS. 7 and 8, the air jets a1 are aligned in a direction offset from the nozzle 20. Furthermore, each of said air jets a1 is directed to be obstructed by collision with at least one other air jet a1 at least at a distance from the liquid jet L being expelled from the nozzle 20, such that a source of turbulence is generated offset from the liquid jet. Thus, multiple sources of turbulence may form a larger area, or volume, of turbulent air in the housing 12. Two air jets a1 form a source of turbulence by collision. In order to avoid direct interaction between the liquid jet 16 and the air jets a1, each source of turbulence, i.e. each obstruction, is configured to be located at least at a distance from the liquid jet. Also, the obstruction is formed so that direct flow from the orifice 26 towards the liquid jet is prevented.

FIGS. 7a-7d show examples of configurations where air jets a1 are arranged to obstruct each other by collision.

FIG. 7a depicts how two pairs of air jets a1 are aligned into another pair of oppositely directed air jets a1. Two sources of turbulence are generated at a distance from the liquid jet L (not shown) being expelled from the nozzle 20.

FIG. 7b shows how two of air jets a1 impinge one another at a distance from the liquid jet L (not shown). Four air jets generate two sources of turbulence at a distance from the liquid jet L being expelled from the nozzle 20. Care is taken to align the air jets a1 such that they do not directly cross the flow path of the liquid jets L being expelled from the apertures of the nozzle 20. In other words, an air jet a1 may pass a part of the nozzle 20 before colliding with another air jet a1, but it may not pass a part of the nozzle comprising the array of apertures.

FIG. 7c shows how an air jet a1 collides with a second air jet a1, which in turn collides with a third air jet a1, and so on. At a point of collision, a source of turbulence is generated, and the impinged air jet proceeds in a turbulent state, shown as an undulating line a1', to impinge another air jet a1.

FIG. 7d shows how two of air jets a1 impinge one another at a distance from the liquid jet L (not shown). Eight air jets generate four sources of turbulence at a distance from the liquid jet L being expelled from the nozzle 20. The configuration is similar to the case shown in FIG. 7b, but here the air jets a1 are all arranged to collide before passing the nozzle 20.

FIG. 8 shows a perspective cross-sectional view of the aerosol generator 10 of FIG. 7a, wherein two orifices 26 are configured to expel air jets a1 towards oppositely directed air jets a1 being expelled from opposite orifices 26.

In the embodiments shown, the liquid jet is directed along the longitudinal axis X (see FIG. 2), which is generally orthogonal to the inlet plane, which inlet plane is consequently substantially parallel with the outlet surface of the nozzle 20. The first inlet guide comprising the orifices 26 is configured to direct the multiple air jets a1 at angles relative to the inlet plane. Preferably, the angle of the air jets is configured for a flow of air generally orthogonal to the flow of the liquid jets, and the orifices 26 are preferably arranged in a plane parallel to the inlet plane. However, other angles of the air jets, in relation to the inlet plane, are conceivable to distribute the sources of turbulence in the housing, not only in a plane around the liquid jets, but also along the flow path of the liquid jets, such that the droplets spend a longer time in the turbulent space before exiting the housing 12.

Furthermore, for a similar purpose, the orifices may be distributed along the axis X to achieve a greater spread of the turbulent space in the housing 12.

In use, the aerosol generator functions as follows. In an exemplary embodiment where the aerosol generator is adapted for a mouthpiece of an inhalation device, a user applies his or her lips to the housing 12 (i.e. the mouthpiece), around the aerosol outlet 17 and activates the device while simultaneously inhaling through the mouthpiece. The activation of the device pressurises the liquid medicament such that it is forced through the apertures of the nozzle 20, exiting the nozzle 20 as at least one liquid jet L. The applied pressure and the apertures are configured such that the liquid jet(s) spontaneously breaks up into a Rayleigh droplet train. During activation, the inhalation of the user generates both the sheath air flow A2 and the turbulence generating air flow A1, wherein the turbulence-generating air flow A1 is directed via orifices 26 to generate sources of turbulence in the vicinity of the liquid jet L, such that the droplets are pulled apart to prevent coalescence of the droplets. Simultaneously, the sheath air flow A2 prevents droplets from adhering to the inner walls of the housing 12.

Similarly, the aerosol generator may also be used for treatment of eye afflictions, in an eye spray device. However, the turbulence-generating air flow A1 and the sheath air flow A2 are necessarily generated by pressurised gas, such as pressurised air, which is actuated by the user at the same time as activating the pressurisation of the liquid medicament.

The invention claimed is:

1. An aerosol generator for a medicament delivery device, the aerosol generator comprising:
    a housing having:
        an inlet part comprising a liquid inlet configured to guide a liquid jet into the housing;
        an air inlet configured to guide an air flow into the housing, wherein the air inlet comprises a first inlet guide for distributing a turbulence-generating air flow and a second inlet guide for distributing a sheath air flow, and wherein the first inlet guide comprises multiple orifices through which said turbulence-generating air flow is configured to be distributed into multiple air jets; and
        an outlet part comprising an aerosol outlet configured to guide an aerosol, comprising liquid mixed with air, out of the housing,
    wherein the air inlet is configured such that each of the multiple air jets entering the housing through the air inlet is obstructed by a physical obstacle positioned between each of the multiple air jets and the liquid inlet at a distance from the liquid jet entering the housing through the liquid inlet, thereby creating multiple sources of turbulence in the housing to interact with droplets of the liquid jet to prevent coalescence of the droplets, each of the physical obstacles formed so that direct flow from the associated orifice towards the liquid jet is prevented.

2. The aerosol generator according to claim 1, wherein the multiple air jets are configured to generate the multiple sources of turbulence distributed in the housing around the liquid jet, each source of turbulence located at least a distance from the liquid jet.

3. The aerosol generator according to claim 2, wherein the liquid jet only indirectly interacts with the turbulence-generating air flow via turbulence generated by the multiple sources of turbulence.

4. The aerosol generator according to claim 1, wherein the air jets are each aligned in a direction orthogonal to the liquid inlet.

5. The aerosol generator according to claim 1, wherein the liquid jet is directed substantially orthogonally to an inlet plane, and wherein the first inlet guide is configured to direct the multiple air jets through the orifices at angles relative to the inlet plane.

6. The aerosol generator according to claim 5, wherein the liquid jet is directed substantially along an axis, and wherein the multiple orifices of the first inlet guide are distributed along the axis.

7. The aerosol generator according to claim 5, wherein the liquid jet is directed substantially along an axis, and wherein the multiple orifices of the first inlet guide are distributed in a plane parallel to the inlet plane.

8. The aerosol generator according to claim 1, wherein the second inlet guide comprises an elongated orifice along an inner perimeter of the housing, which elongated orifice is configured to distribute a sheath air flow along an inner surface of the housing in a direction towards the aerosol outlet.

9. The aerosol generator according to claim 1, wherein the liquid inlet is comprised by a nozzle having a micro-structured aperture configured to generate a liquid jet in the form of a Rayleigh droplet train from a pressurised liquid which is forced through said aperture.

10. The aerosol generator according to claim 9, wherein the nozzle comprises multiple micro-structured apertures for generating multiple Rayleigh droplet trains.

11. The aerosol generator according to claim 1, wherein the housing is arranged in a mouthpiece of an inhalation device and wherein the turbulence-generating air flow and the sheath air flow are configured to be generated by a user inhaling air through the mouthpiece.

12. The aerosol generator according to claim 1, wherein the housing is arranged in an eyepiece of an eye spray device.

13. The aerosol generator according to claim 12, wherein the turbulence-generating air flow and the sheath air flow are configured to be generated by pressurised air actuated by a user.

14. An aerosol generator for a medicament delivery device, the aerosol generator comprising:
    a housing having an inlet part;
    a nozzle configured to generate a liquid jet into the housing, the nozzle being arranged on the inlet part of the housing; and
    an air inlet configured to guide an air flow into the housing, wherein the air inlet comprises a first inlet guide for distributing a turbulence-generating air flow and a second inlet guide for distributing a sheath air flow, and wherein the first inlet guide comprises multiple orifices through which said turbulence-generating air flow configured to be is distributed into multiple air jets,
    wherein the housing further has an aerosol outlet configured to guide an aerosol, comprising liquid mixed with air, out of the housing, and
    wherein the air inlet is configured such that each of the multiple air jets is directed to be obstructed by collision with a physical obstacle positioned between each of the multiple air jets and the nozzle at a distance from said liquid jet, thereby creating multiple sources of turbulence in the housing to interact with droplets of the liquid jet to prevent coalescence of the droplets, each of the physical obstacles formed so that direct flow from the associated orifice towards the liquid jet is prevented.

15. The aerosol generator according to claim 14, wherein the air inlet further comprises an elongated orifice along an inner perimeter of the housing, wherein the elongated orifice is configured to distribute the air flow into the sheath air flow along an inner surface of the housing in a direction towards the aerosol outlet.

16. The aerosol generator according to claim 14, wherein the housing is arranged in a mouthpiece of an inhalation device or an eyepiece of an eye spray device, wherein the air flow is configured to be generated by pressurised air actuated by a user.

\* \* \* \* \*